US006235218B1

(12) United States Patent
Annen et al.

(10) Patent No.: US 6,235,218 B1
(45) Date of Patent: *May 22, 2001

(54) PROCESS FOR PREPARING N-ALKYL AMMONIUM ACETONITRILE COMPOUNDS

(75) Inventors: Ulrich Annen, Hassloch (DE); James E. Deline, Livermore, CA (US); Lafayette D. Foland, Dublin, CA (US); Kevin A. Klotter, Livermore, CA (US); Josef Müller, Grosskarlbach (DE); Michael Müller, Biblis (DE); Klaus Mundinger, Limbergerhof (DE); Martin A. Phillippi, Pleasanton, CA (US); Alfred Ruland, Schriesheim (DE); Wolfgang Schäfer, Weisenheim am Berg (DE); Gregor Schürmann, Schwetzingen (DE); Rudi Widder, Leiheim (DE); Alfred G. Zielske, Pleasanton, CA (US)

(73) Assignee: The Clorox Company, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/444,041

(22) Filed: Nov. 19, 1999

Related U.S. Application Data

(63) Continuation of application No. 08/905,511, filed on Aug. 4, 1997, now abandoned, which is a continuation of application No. 08/758,542, filed on Nov. 29, 1996, now abandoned, which is a continuation-in-part of application No. 08/475,292, filed on Jun. 7, 1995, now Pat. No. 5,739,327.

(51) Int. Cl.[7] ..................... C07D 265/30; C07D 295/00; C09K 3/00
(52) U.S. Cl. ................... 252/186.39; 544/163; 544/402; 544/86; 510/312
(58) Field of Search .......................... 544/86, 163, 402; 252/186.39; 546/246

(56) References Cited

U.S. PATENT DOCUMENTS

| | | | |
|---|---|---|---|
| 2,425,693 | 8/1947 | Cook et al. | 558/459 |
| 2,489,950 | 11/1949 | Blicke | 546/205 |
| 2,625,547 | 1/1953 | Lawson et al. | 544/171 |
| 2,774,758 | 12/1956 | Yanko | 544/163 |
| 2,848,450 | 8/1958 | Rudner et al. | 544/163 |
| 2,851,458 | 9/1958 | Billinghurst | 594/163 |
| 2,868,786 | 1/1959 | Siemer et al. | 544/171 |
| 3,532,735 | 10/1970 | Morgan | 558/455 |
| 3,689,470 | 9/1972 | Shachat et al. | 576/312 |
| 3,772,275 | 11/1973 | Hernestam et al. | 544/169 |
| 3,780,092 | 12/1973 | Samour et al. | 560/222 |
| 3,873,583 | 3/1975 | Walz et al. | |
| 3,882,035 | 5/1975 | Loffelman et al. | 510/313 |
| 4,086,175 | 4/1978 | Kravetz et al. | 510/314 |
| 4,134,889 | 1/1979 | Distler et al. | 546/230 |
| 4,164,511 | 8/1979 | Distler et al. | 558/346 |
| 4,199,466 | 4/1980 | Benson, Jr. | 510/314 |
| 4,215,003 | 7/1980 | Finley et al. | 8/111 |
| 4,328,226 | 5/1982 | Witek et al. | 514/239.5 |
| 4,342,872 | 8/1982 | Grier et al. | 546/186 |
| 4,397,757 | 8/1983 | Bright et al. | 252/186.41 |
| 4,551,526 | 11/1985 | Mai et al. | 544/163 |
| 4,737,498 | 4/1988 | Banasiak et al. | 514/237.8 |
| 4,751,015 | 6/1988 | Humphreys et al. | 544/139 |
| 4,904,406 | 2/1990 | Darwent et al. | |
| 4,915,863 | 4/1990 | Aoyagi et al. | 510/376 |
| 4,921,631 | 5/1990 | Gradwell et al. | 252/186.38 |
| 4,978,770 | 12/1990 | Aoyagi et al. | 558/455 |

(List continued on next page.)

FOREIGN PATENT DOCUMENTS

| | | |
|---|---|---|
| P25035829 | 1/1975 | (DE) . |
| P25557691 | 12/1975 | (DE) . |
| P26204455 | 5/1976 | (DE) . |
| 20303520 | 8/1988 | (EP) . |
| 883075582 | 8/1988 | (EP) . |
| 912011707 | 5/1991 | (EP) . |
| 912012606 | 5/1991 | (EP) . |
| 0790244 | 2/1997 | (EP) . |
| 62-225871 | 9/1987 | (JP) . |
| 63-167157 | 7/1988 | (JP) . |
| 1230773 | 9/1989 | (JP) . |
| 6136391 | 10/1992 | (JP) . |
| 96/07650 | 3/1996 | (WO) . |

OTHER PUBLICATIONS

Derwent, Abstract Accession No. 96–140373 taken from DE 4431212, published Mar. 7, 1996, entitled: "Prepn. of water–insensitive quaternised glycine nitrile derivs. by one-–pot method, by reacting amine with mono or di aldehyde and cyanide in aq. medium and adding alkylating atent".*

(List continued on next page.)

Primary Examiner—Joseph D. Anthony
(74) Attorney, Agent, or Firm—J. Suzanne Siebert; Joel J. Hayashida

(57) ABSTRACT

A process is provided for the preparation of a compound having the structure of Formula I

FORMULA I

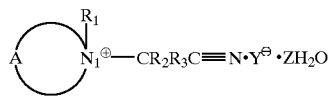

The process includes reacting a heterocyclic amine with a monoaldehyde or a dialdehyde in a pH range of from about 8 to 14 and then quaternizing the so-reacted heterocyclic amine with an alkylating agent at a pH of not less than about 2. The use of pH control substantially prevents formation of an undesirable protonated reaction intermediate.

9 Claims, No Drawings

U.S. PATENT DOCUMENTS

| | | | |
|---|---|---|---|
| 5,093,022 | 3/1992 | Sotoya et al. | 510/376 |
| 5,106,528 | 4/1992 | Francis et al. | 252/186.23 |
| 5,236,616 | 8/1993 | Oakes et al. | 510/376 |
| 5,281,361 | 1/1994 | Adams et al. | 252/186.38 |
| 5,330,677 | 7/1994 | Sotoya et al. | 252/186.38 |
| 5,399,746 | 3/1995 | Steiger et al. | 560/251 |
| 5,405,412 | 4/1995 | Willey et al. | 8/111 |
| 5,460,747 | 10/1995 | Gosselink et al. | 252/186.38 |
| 5,591,378 | 1/1997 | Deline et al. | 252/186.38 |
| 5,739,327 * | 4/1998 | Arbogast et al. | 544/402 |
| 5,741,437 * | 4/1998 | Arbogast et al. | 252/186.39 |
| 5,877,315 * | 3/1999 | Deline et al. | 544/86 |
| 5,958,289 * | 9/1999 | Arbogast et al. | 252/186.39 |
| 5,959,104 * | 9/1999 | Arbogast et al. | 544/163 |
| 6,017,464 * | 1/2000 | Deline | 252/186.39 |

OTHER PUBLICATIONS

Hart et al., "Some New Quaternary–Substituted Alkyl Morpholinium Chlorides and Pyrrolidinium Alkyl Sulfates," *Journal of Organic Chemistry*, 22:1 (Mar. 5, 1957), pp. 86–88.

Gubanova et al., "Synthesis and Antiviral Activity of Organic and Organophosphorus Derivatives of α–Aminonitriles," translated from *Khimiko–farmatsevticheskii Zhurnal*, 26, No. 7–8, pp. 60–62 (1992).

Stanley et al., "Synthesis and Enzymatic Evaluation of Some N–Alkyl Branched Chain Piperidine Salts and N–Alkyl–3–(N,N–diethylcarbamoyl)piperidine Salts as Inhibitors of Acetyl– and Butyrylcholinesterase," *J. Medicinal Chemistry*, 17, No. 1, (1974).

Lespagnol et al., "Guanidines monosubstituées à fonction ammonium quaternaire," *Mèmoires Prèsentès a la Socièt è Chimique*, paper presented at the Congress of the International Pharmaceutical Federation, Zurich, Sep. 1959, and the English translation of Lespagnol et al. reference, cited above as "C4."

Menschutkin, N., "Beiträge zur Kenntnis der Affinitätskoeffizienten der Alkylhaloid und der organischen Amine," *Z. Physik. Chem.*, 5, 589 (1890).

Menschutkin, N., "Uber die Affinitätskoeffizienten der Alkylhaloid und der Amine," *Z. Physik. Chem*, 5, 589 (1890).

Abraham, M.H., "Solvent Effects on Transition States and Reaction Rates," in *Progress in Physical Organic Chemistry*, 11, (eds. Streitwieser and Taft), 1 (1974).

Arnett and Reich, "Electronic Effects on the Menschutkin Reaction. A Complete Kinetic and Thermodynamic Dissection of Alkyl Transfer to 3– and 4–Substituted Pyridines," *J. Am. Chem. Soc.*, 102, 5892 (1980).

* cited by examiner

PROCESS FOR PREPARING N-ALKYL AMMONIUM ACETONITRILE COMPOUNDS

This is a continuation of application Ser. No. 08/905,511, filed Aug. 4, 1997, now abandoned; which was a continuation application of Ser. No. 08/758,542, filed Nov. 29, 1996, now abandoned; which was a continuation-in-part application of Ser. No. 08/475,292, filed Jun. 7, 1995, now U.S. Pat. No. 5,739,327, issued Apr. 14, 1998.

FIELD OF THE INVENTION

The present invention generally relates to N-alkyl ammonium acetonitrile compounds useful in applications such as bleaching and cleaning and particularly relates to a process for the preparation of such compounds.

This application is a continuation in part of Ser. No. 08/475,292, filed Jun. 7, 1995, entitled "N-ALKYL AMMONIUM ACETONITRILE BLEACH ACTIVATORS," inventors Arbogast et al., of common assignment herewith.

BACKGROUND OF THE INVENTION

Peroxy compounds are effective bleaching agents, and compositions including mono- or di-peroxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid can present a problem of storage stability for compositions consisting of or including peroxyacids.

One approach to the problem of reduced bleaching activity of peroxyacid compositions has been to include activators of hydrogen peroxide or an active oxygen source. U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester.

Other examples of activators include tetraacetyl ethylenediamine (TAED), nonanoyloxy benzene-sulfonate (NOBS), and nonanoylglycolate phenol sulfonate (NOGPS). NOBS and TAED are disclosed, for example, in U.S. Pat. No. 4,417,934, Chung et al., and NOGPS is disclosed, for example, in U.S. Pat. No. 4,778,618, Fong et al., the disclosures of which are incorporated herein by reference.

Thus, U.S. Pat. No. 4,778,618, Fong et al., issued Oct. 18, 1988 provides novel bleaching compositions comprising peracid precursors with the general structure

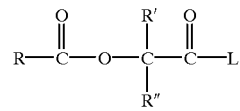

wherein R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $N^+R_3^\alpha$, wherein $R^\alpha$ is $C_{1-30}$ alkyl; and where L is a leaving group which can be displaced in a peroxygen bleaching solution by peroxide anion. U.S. Pat. No. 5,182,045, issued Jan. 26, 1993, and U.S. Pat. No. 5,391,812, issued Feb. 21, 1995, inventors Rowland et al. are similar, but are polyglycolates of the Fong et al. monoglycolate precursors, or activators.

U.S. Pat. No. 4,915,863, issued Apr. 10, 1990, inventors Aoyagi et al., discloses compounds said to be peracid precursors that have nitrile moieties. U.S. Pat. No. 5,236,616, issued Aug. 17, 1993, inventors Oakes et al., discloses compounds said to be cationic peroxyacid precursors that have nitrile moieties. These nitrile containing activators do not contain a leaving group, such as the Fong et al. leaving groups, but instead include a quaternary ammonium group suggested as activating the nitrile and said, upon reaction or perhydrolysis in the presence of hydrogen peroxide, to generate a peroxy imidic acid as bleaching species. The Aoyagi et al. activators include an aromatic ring, which tends to cause fabric yellowing.

German patent application P4431212.1, published Mar. 7, 1996 describes production of quaternized glycinonitriles in the form of stable aqueous solutions.

New peroxygen activators that provide excellent bleaching and that can be formulated for liquid or solid compositions remain desirable for applications such as laundry and household bleaching and cleaning.

SUMMARY OF THE INVENTION

In one aspect of the present invention, nitrites are provided in substantially solid form having the structure of Formula I

FORMULA I

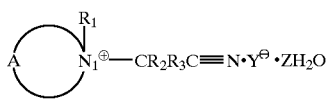

wherein A is a saturated ring formed by five atoms in addition to the $N_1$ atom, the five saturated ring atoms being four carbon atoms and a heteroatom, the substituent $R_1$ bound to the $N_1$ atom of the Formula I structure including either (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-24}$, or (e) —$CR_2R_3C\equiv N$ where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$.

The Formula I compounds have a quaternary nitrogen atom ($N_1$), requiring the presence of at least one counterion (Y) to be associated therewith, which is illustrated in Formula I as "$Y^\ominus$," but as understood can be monovalent, or multivalent. Y includes counterions, or organic and inorganic anions, such as chloride, bromide, nitrate, alkyl sulfate, bisulfate, sulfate, tosylate, and mesylate. Especially preferred are methyl sulfate, sulfate, bisulfate, tosylate, and mixtures thereof. Z will be in the range of 0 to 10. These compounds, or salts, are particularly well suited to granule bleaching and cleaning compositions.

The nitriles with the Formula I structure are particularly useful when formulated as compositions that include a source of active oxygen, and these compositions provide excellent bleaching in alkaline solutions.

Preferred embodiments include lower alkyls substituted at the $N_1$, e.g. N-methyl morpholinium acetonitrile, N-ethyl morpholinium acetonitrile, N-butyl morpholinium acetonitrile, which are illustrated by Formula II (with "n" preferably being 0 to 24 and where "Y" is one of the above described counterions).

FORMULA II

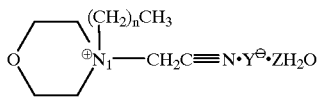

A particularly preferred embodiment is an N-methyl morpholinium acetonitrile salt where "n" of Formula II is 0. In the preferred process for preparing the Formula I or Formula II compounds, decomposition of a process intermediate is substantially avoided so as to reduce amounts of undesired free hydrogen cyanide, preferably to below the analytical detection limit. In a preferred embodiment of the process, a compound with the structure of Formula II is prepared to be substantially free of hydrogen cyanide by reacting morpholine with a monoaldehyde or a dialdehyde and hydrogen cyanide or an alkali metal cyanide in an aqueous medium (Step A) and then with an alkylating agent (Step B), whereby Step A is carried out in a pH range of from 8 to 14 and Step B is carried out at a pH of not less than about 2. Most preferably, Step B is carried out at a pH of not less than about 3.

Compositions including these nitriles are useful, for example, in laundry products, such as bleaching additives, detergents, detergent boosters, detergents with bleach, bleaches, bleaching aids, stain removers, and spot treatment products such as stain removers, prewash and presoak laundry aids. Among the advantages derived from such compositions are improved cleaning, stain removal, spot removal, whitening, and brightening of treated articles.

DETAILED DESCRIPTION OF THE PREFERRED EMBODIMENTS

Application Ser. No. 08/475,291, filed Jun. 7, 1995, entitled "N-Alkyl Ammonium Acetonitrile Bleach Activators," describes nitrites, typically quaternized, for which a preferred embodiment was N-methyl ammonium acetonitrile methylsulfate, to which this application relates. There are several aspects of the present invention.

One aspect is wherein novel quaternized nitriles are provided having certain counterions which result in substantially reduced hygroscopicity (with respect to amorphous N-methyl ammonium acetonitrile methylsulfate, or MMAMS). Another aspect is wherein novel nitrites are provided as granules by being carried, coated, or admixed with a suitable particulate material. These granules have improved stability and/or reduced hygroscopic characteristics with respect to amorphous MMAMS. Yet another aspect of the invention is for an improved process of making novel quaternized nitrites so as to have reduced amounts of undesired by-product.

All these inventive aspects have as a common element certain novel nitrites with the structure generally illustrated by Formula I. The $N_1$ atom of the Formula I compound is part of a saturated ring, illustrated by "A" in Formula I.

FORMULA I

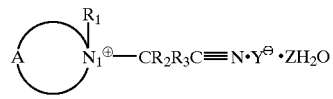

This saturated ring of which $N_1$ is a part has a plurality of atoms. The saturated ring illustrated by ring "A" in Formula I preferably has at least one hetero atom in the saturated ring in addition to the $N_1$, more preferably wherein the ring includes an oxygen atom, a sulfur atom, or one or two additional nitrogen atoms.

The at least one nitrogen in the saturated ring ($N_1$) shown in Formula I is N-acetonitrile substituted and also quaternized. Without being bound by theory, the electron withdrawing nature of the quaternary nitrogen may be increased by being part of a saturated, heterocyclic ring and may also function to improve the hydrophilic character of the oxidant.

A substituent $R_1$ will be bonded to the $N_1$ atom of the Formula I structure and additionally a nitrile moiety ($-CR_2R_3C\equiv N$) is bonded to the $N_1$ atom, where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. The $R_1$ substituent may be a $C_{1-24}$ alkyl or alkoxylated alkyl where the alkoxy is $C_{2-4}$, $C_{4-24}$ cycloalkyl, a $C_{7-24}$ alkaryl, a repeating or nonrepeating alkoxy or alkoxylated alcohol, where the alkoxy unit is $C_{2-4}$, and illustrative such groups are, for example,

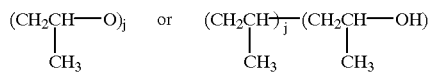

where j=1 to 24. The $R_1$ substituent may also be another $-CR_2R_3C\equiv N$, and again $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$, and illustrative such groups are:

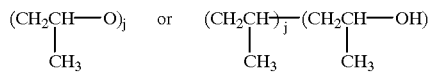

where j=1 to 24.

Particularly preferred, saturated rings forming the cyclic configuration A of Formula I contain six atoms including the $N_1$ atom, but the number of atoms forming the cyclic configuration can range from 3 to 9. When two heteroatoms are present with the cyclic configuration A of Formula I, then a three member ring is unusual; but, for the cyclic configuration B of Formula III shown below, where there may only be $N_1$ as the sole heteroatom, then three membered rings are very likely.

As already noted, the particularly preferred saturated ring of which $N_1$ is a part has five atoms in addition to $N_1$, with at least one hetero atom being in the saturated ring in addition to the $N_1$, preferably wherein the heteroatom of the ring is an oxygen atom or a sulfur atom, most preferably where the heteroatom is oxygen.

Particularly preferred activator embodiments are illustrated by Formula II (where "Y" and "Z" will be hereinafter described, and "n" is 0 to 24).

FORMULA II

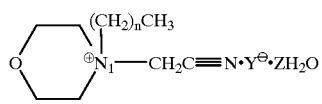

Derivatives of the Formulas I and II nitriles include peroxyimidic intermediates that are believed formed from the nitrites in the presence of an active oxygen source. So formed, peroxyimidic derivatives typically would be short-lived intermediates formed in situ when the nitrites of the invention interact with a source of hydrogen peroxide and where the reactive nitrile moiety forms a peroxyimidic acid. However, such peroxyimidic derivatives may also be prepared in situ by analogy to syntheses known in the art.

Counterions

Since the novel nitrile compounds are normally quaternized, they will include at least one counterion (designated as "Y"). Suitable counterions are monovalent or multivalent and include tosylates, lower alkyl tosylate (e.g. methyl tosylate and ethyl tosylate), and mesylates. Further, in the earlier noted copending application Ser. No. 08/475,292, filed Jun. 7, 1995, N-alkyl ammonium acetonitrile compounds are disclosed as typically including a wide variety of counterions such as chloride, bromide, nitrate, alkyl sulfate, and the like, and wherein a preferred embodiment was described therein as N-methyl ammonium acetonitrile methylsulfate.

When one chooses the granule aspect of this invention, then such a wide variety of counterions remain available in choosing which counterion may be desired, including methylsulfate as counterion. This is because most of the granule embodiments protect stability of the nitrile (for example, against humidity during storage). However, the novel nitrile compounds need not be in granule form in order to be suitable for many applications and to provide compounds stabilized against moisture pick-up.

One particularly preferred embodiment herein is where the counterions are either sulfate, bisulfate, or mixtures thereof. Such a sulfate or bisulfate salt (or mixtures thereof) may be produced from heated and acidified N-methyl morpholinium acetonitrile methylsulfate, or MMAMS (wherein the counterion before the conversion to bisulfate or sulfate is methylsulfate). These two particularly preferred salts are illustrated by Formula IIIA and IIIB. A third particularly preferred salt, N-methyl morpholinium acetonitrile tosylate ("MMATS"), is illustrated by Formula IIIC.

FORMULA III

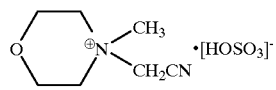

MMABS

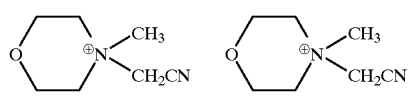

MMAS

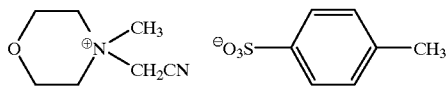

MMATS

The MMABS, MMAS, and MMATS embodiments are particularly useful where one wishes a substantially solid composition to have reduced hygroscopicity with respect to MMAMS. Although the MMABS, MMAS, and MMATS embodiments may also be in granule form, they need not be, and are usable in crystalline or amorphous forms.

The sulfate and bisulfate counterions are in equilibrium with one another in solution, and the predominant species is dependent on the solution pH. Above pH 2, the sulfate group predominates, while below pH 2 the bisulfate form predominates. Thus, the particular form desired may be obtained by controlling the solution pH, although a mixture is obtained at an intermediate pH.

However, the particularly preferred embodiment is where granules are provided in which the nitrile salt is bisulfate that has been crystallized, the crystals redissolved, and the solution (thus having impurities removed) is granulated.

Nitrile Water Content

The novel nitriles may exist either as anhydrous salts (essentially free of water) or as stable hydrates having discrete amounts of water of hydration. Thus, in Formulas I and II, Z is in the range of 0 to 10, preferably 0 to 6, and most preferably 0 to 1. This "Z" may be viewed as an average number of moles of hydration. Because there may be mixtures of the Formulas I and II compounds with integer numbers of moles of hydration, the actual value for Z may be a non-integer value. The value for Z may be reduced when one converts a crystalline or amorphous form of novel nitrile into a granulated form.

Physical Form of Nitriles

Amorphous forms of the Formulas I and II nitrites may be obtained by rapid evaporation or precipitation from solutions (such as in spray drying, column drying, and the like). Alternatively, crystalline salts may be obtained by crystallization or careful evaporation, which crystalline forms tend to be less hygroscopic than amorphous forms. This reduced hygroscopicity of the crystalline salts is believed, without being bound to theory, due to the tight packing of the molecules within the crystal that prevent bulk water penetration and the reduced total surface area of a crystalline solid compared to an amorphous form of the same solid. Granule embodiments may also be prepared from the nitrites in either the crystallized or amorphous forms.

Surprising Advantages of the Manufacturing Process

Because the preparation of nitrites can generate intermediates (believed to be a protonated morpholine reaction intermediate when morpholine is used in preparing the Formula II compounds) that can decompose to undesirable free hydrogen cyanide, a process for producing the nitrites in which free hydrogen cyanide is virtually no longer detectable is highly desirable. Practice of the inventive process is successful in reducing the values for free hydrogen cyanide from less than about 5 ppm to 0 (wherein 0 signifies as being below the analytical detection limit).

Bleaching and Cleaning Compositions

Bleaching and cleaning compositions of the invention include the Formula I nitrile salts as activator, together with a source of active oxygen.

The peroxide or active oxygen source for compositions of the invention may be selected from the alkaline earth metal salts of percarbonate, perborate, persilicate and hydrogen peroxide adducts and hydrogen peroxide. Most preferred are sodium percarbonate, sodium perborate mono- and tetrahydrate, and hydrogen peroxide. Other peroxygen sources may be possible, such as monopersulfates and monoperphosphates, or their equivalent aqueous forms, such as monopersulfuric acid, known in the trade as Caro's acid or Caroate, a product of BASF AG, Germany.

The range of peroxide to activator is preferably determined as a molar ratio of peroxide to activator. Thus, the range of peroxide to each activator is a molar ratio of from about 0.1:1 to 100:1, more preferably about 1:1 to 10:1 and most preferably about 2:1 to 8:1. This peracid activator/peroxide composition should provide about 0.5 to 100 ppm A.O., more preferably about 1 to 50 ppm peracid A.O. (active oxygen), and most preferably about 1 to 20 ppm peracid A.O., in aqueous media for typical laundry applications. Formulations intended for hard surface cleaning will more typically have peracid activator/peroxide providing from about 0.5 to 1,000 ppm A.O., more preferably about 1 to 500 ppm peracid A.O., and most preferably about 1 to 200 ppm peracid A.O.

Compositions of the invention have been found to provide superior bleaching (cleaning and stain removal) benefits on common laundry stains.

Granular Embodiments and Delivery Systems

The substantially solid salt activators can be directly used in a crystalline or amorphous form, for example by incorporating into a solid matrix in solid detergent bleaches. As will be hereinafter more fully described, preparation of the novel nitrites in bisulfate or sulfate form will typically be by converting from another counterion (e.g. methylsulfate). The conversion may be complete or partial. Thus, a Formula I or II salt composition may include from about 1 wt. % to about 99 wt. % of another compound related to the Formula I compound, but differing therefrom in counterion. The degree of conversion to bisulfate or sulfate will be directly related to the amount of hygroscopicity reduction of such a salt composition.

Whether converted to bisulfate or sulfate or not, incorporation of the novel nitrile salts into dry, or granulated, formulations can be achieved through several different embodiments. Granulated formulations hold several advantages over liquid formations, such as for example, reduced shipping costs. Other advantages are an increased stability of the nitrile activator against moisture, alkalinity (e.g. carbonate), against premature activation, and reduction in possible dye damage.

Typically, the precursor composition before granulation is of sprayable consistency, that is to say, in the form of a melt, suspension, or solution. One suitable process for granulation may be performed in a fluid bed or rotatory drum agglomerator, such as is described by U.S. Ser. No. 08/554,672, filed Nov. 8, 1995, entitled "Agglomerated Colorant Speckle Exhibiting Reduced Colorant Spotting," incorporated herein by reference.

In the granular embodiments the nitrile salts can be carried by, coated with or admixed with a solid particulate, such as an inert, porous material. These granules can further have a coating that is sufficient to delay dissolution in aqueous solution. For example, appropriate such coatings include surfactants, waxes, polymers, or melts thereof, and dusting or flow agents such as silicas and silicates. The coatings can encapsulate the nitrile-containing core.

Granules preferably have an average particle size of from about 3 nm to about 2 mm. For example, activators of the invention can be dispersed onto a solid or granulated carrier such as silica gel, silicic acid, silicate, aluminum oxide, kaolin, aluminum silicate, mixtures or other carriers such as clay, zeolite, organic polymers including starch and ion exchange material. Additional solids useful for carriers include alkali metal and alkaline earth salts of carbonate, bicarbonate, sesquicarbonate, phosphate, chloride, sulfate, bisulfate, and borate.

A high internal surface area of the carrier materials is preferred for such a granular embodiment. The total surface area preferably lies in the range from 10 to 500 $m^2/g$ or, especially, 100 to 460 $m^2/g$ or, especially, 250 to 450 $m^2/g$.

Although most conventional types of chemically inert, porous materials can be used as carrier materials, silicic acids, silicates, precipitated silicas, aluminum oxides, various varieties of clays or aluminum silicates or mixtures thereof are preferred.

Silica gels (silica gels, silicic acid gels) are colloidal, formed or unformed silicic acids of elastic to solid consistency with a loose to compact pore structure and a high adsorption capacity. Silica gel surfaces usually exhibit acidic properties. Silica gel is usually manufactured from waterglass by reaction with mineral acids. Precipitated silicas are powders obtained by coagulation of silica particles from an aqueous medium under the influence of coagulants.

Among the silicic acids, thermally generated silicic acids, i.e. highly dispersed "pyrogenic" $SiO_2$ qualities (e.g. the Aerosils® or Cab-o-Sils®) that are usually prepared by flame hydrolysis of $SiCl_4$ can be used especially advantageously in addition to silicic acids that are obtained in accordance with the wet process. In a specially preferred form of embodiment of the present invention, use is made of silicic acid with an average (agglomerate) particle size of 100 nm or 30 mm or, especially, 100 $\mu$m to 1.5 mm and a $SiO_2$ content of 95 to 100% by weight or, preferably, 98 to 100% by weight. In addition, precipitated silicone, such as SIPERNAT® silica material can be used advantageously.

Aluminum oxides occur in nature in, for example, the form of argillaceous earth or as corundum. In this regard, the aluminum oxide is present in the $\alpha$-modification. Industrially, $\alpha$-$Al_2O_3$ is obtained from bauxite using the Bayer process. Suitable "active" aluminum oxides with a high specific surface area are prepared in the form of adsorbents, via precipitation procedures, from aluminum salt solutions or via the calcination of $\alpha$-aluminum hydroxide.

Clays are naturally occurring crystalline and amorphous hydrated silicates of aluminum, iron, magnesium, calcium, potassium, and sodium. These clays may also contain amounts of aluminum oxides and silica. Useful clays may include kaolins, serpentines, talcs, pyrophyllites, attapulgites, sepiolites, montmorillonites, and bauxitic clays. These clays may undergo various processes before use. For example, clays may be air-floated, water-washed, calcined, delaminated, acid activated, or treated with dispersants.

A preferred process for providing an aluminum silicate carrier particle is disclosed by Ser. No. 08/554,672, noted above, which process can also be used for providing a carrier for a pigment or other colorant. Aluminum silicates are compounds with different proportions of $Al_2O_3$ and $SiO_2$. Aluminum silicate minerals in which Al occupies lattice positions in the crystal lattice in the place of Si are the aluminosilicates (e.g. the various varieties of ultramarine, zeolite, and feldspar). Freshly precipitated aluminum silicates are finely dispersed and have a large surface area and a high adsorption capacity. Among useful aluminosilicates are synthetic zeolites commonly used as detergent builders.

The ratio of nitrile salt and carrier materials in a solid composition. in accordance with the invention can vary within certain limits, depending on the method of manufacturing the solid composition and the properties of the carrier, and the final end use. A preferred ratio is 10 to 95 parts by weight of the nitrile to 5 to 90 parts by weight of the carrier, especially 10 to 70 parts of weight of the nitrile to 10 to 70 parts by weight of the carrier. A ratio of 50 to 90 parts by weight of Formula I to 10 to 50 parts by weight of carrier is especially preferred where the desire is to maximize the concentration of active Formula I. A ratio of 50 to 10 parts by weight of Formula I to 10 to 90 parts by weight of carrier is especially preferred where the desire is to disperse the active Formula I, for instance to reduce localized bleaching. The indicated parts by weight are based on the anhydrous solid. For example, granules of the invention may include one surfactant or a mixture of surfactants so as to constitute an amount preferably of about 0.5 to about 50 parts by weight.

Surfactants of Delivery Systems

As earlier mentioned, compositions of the invention frequently desirably contain varying amounts of surfactants, which may act both as a cleaning active agent as well as also to help disperse sparingly soluble materials in liquid phase when the compositions are put to use.

Surfactants with which the activators and active oxygen compositions may be combined or admixed include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides, phosphine oxides, sulfoxides and their ethoxylated derivatives.

Anionic surfactants may also be suitable. Examples of such anionic surfactants may include the ammonium, substituted ammonium (e.g., mono-di-, and triethanolammonium), alkali metal and alkaline earth metal salts of $C_6$–$C_{20}$ fatty acids and rosin acids, linear and branched alkyl benzene sulfonates, alkylethoxylated ether sulfates, alkylethoxylated or propoxylated ether sulfates, alkyl sulfates, alkyl ether sulfates, alkane sulfonates, alpha olefin sulfonates, hydroxyalkane sulfonates, fatty acid monoglyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear inert substituents such as phenyl groups.

Suitable amphoteric and zwitterionic surfactants containing an anionic water-solubilizing group, a cationic group or a hydrophobic organic group include amino carboxylic acids and their salts, amino dicarboxylic acids and their salts, alkyl-betaines, alkyl aminopropylbetaines, sulfobetaines, alkyl imidazolinium derivatives, certain quaternary ammonium compounds, certain quaternary phosphonium compounds and certain tertiary sulfonium compounds.

Other common detergent adjuncts may be added if a bleach or detergent bleach product is desired. Table 1 illustrates dry bleaching composition embodiments incorporating the Formula I salts.

TABLE 1

| COMPONENT | COMPONENT RANGES (Wt. %) |
|---|---|
| Surfactant: | |
| Linear alkyl benzene sulfonate (LAS) | 0–15 |
| Alkyl Sulfate (AS) | 0–15 |
| Alcohol ethoxy sulfate (AEOS) | 0–15 |
| Alcohol ethoxylate (AE) | 0–15 |
| Builder: | |
| Sodium carbonate | 20–70 |
| Zeolite | 0–50 |
| Polyacrylate polymer | 0–5 |
| Sodium silicate | 0–8 |
| Filler: | |
| Sodium chloride | 0–30 |
| Sodium sulfate | 0–30 |
| Water | 0–5 |
| Bleaching System: | |
| Sodium perborate monohydrate | 4–40 |
| MMA[1] activator | 1–10 |
| Other: | |
| Enzyme(s)[2] | 0–3 |
| Brightener | 0–2 |
| Dye/Pigment | as needed |
| Perfume | as needed |

[1]Inventive nitrile, preferably MMAMS, MMAS, MMABS, or MMATS.
[2]Examples include but are not limited to protease, amylase, lipase, cellulase (alone or in combinations)

Sources of Acid/Alkali

Compositions of the invention, when combined with a source of active oxygen, preferably function for bleaching best at an alkaline pH, but are shelf stabilized best at an acidic pH, particularly a pH of from 0–5, more preferably 0–2, most preferably 0–1. Thus, compositions of the invention preferably include a source of protons as an "acid sink." This can be achieved, for example, by adding acid, preferably at levels from about 0–50 wt. % of final solid weight to liquid containing the nitrites prior to any further granulation processing (mixing or drying). Preferred acids include citric acid, sulfuric acid, succinic acid, hydrochloric acid, sulfurous acid, aryl sulfonic acids and alkyl aryl sulfonic acids, as well as polyacrylic acid, maleic acid, nitric acid, and sulfamic acid. Most preferred are sulfuric acid and sulfurous acid.

When the composition is ready for use, it is especially advantageous to have an amount of alkaline buffer present sufficient to maintain a pH greater than about 8, more preferably in the range of about 8.5 to about 10.5 for most effective bleaching, when the granules are dissolved or dispersed into an aqueous wash system. If used as a hard surface cleaner, on the other hand, it may be useful to co-dispense the alkaline buffer in a separate, preferably liquid, composition. These alkaline buffers include, but are not limited to, alkali metal hydroxides (sodium, lithium, potassium), ammonium hydroxide, alkali metal and ammonium carbonates, alkali metal and ammonium carbamates, alkali metal and ammonium polyacrylates, alkali metal and ammonium succinates, alkali metal and ammonium maleates and additional conjugate bases of weak organic acids, such as those mentioned hereinabove. Further, organic bases are included, such as, without limitation, ethanolamine, diethanolamine, triethanolamine, hydroxyamine, methylamine, dimethylamine, and trimethylamine.

Additional Functional/Aesthetic Adjuncts

Other adjuncts (useful in cleaning and laundering applications) are optionally included in the inventive compositions. Dyes include anthraquinone and similar blue dyes. Pigments may also be used, and can have a bluing effect by depositing on fabrics washed with a detergent bleach containing UMB. Monastral colorants are also possible for inclusion. Brighteners or whiteners, such as stilbene, styrene and styrylnaphthalene brighteners (fluorescent whitening agents), may be included. Fragrances used for aesthetic purposes are commercially available from Norda, International Flavors and Fragrances, and Givaudon. Stabilizers include hydrated salts, such as magnesium sulfate, and boric acid.

In some of the compositions herein, adjuvants include (and are especially preferred) a chelating agent or sequestrant, and preferably a non-phosphate containing sesquesterant, and most preferably, an aminopolyphosphonate. These chelating agents assist in maintaining the solution stability of the salt activators and active oxygen source in order to achieve optimum performance. In this manner, they are acting to chelate heavy metal ions, which cause catalyzed decomposition of the active oxygen source and of the (believed) in situ formed peroxyimidic acids, although this is a non-binding theory of their action and not limiting.

The chelating agent is selected from a number of known agents which are effective at chelating heavy metal ions. The chelating agent should be resistant to hydrolysis and rapid oxidation by oxidants. Preferably, it should have an acid dissociation constant (pKa) of about 1–9, indicating that it dissociates at low pH's to enhance binding to metal cations. Acceptable amounts of the (optional) chelating agent range from 0–1,000, more preferably 5–500, most preferably 10–100 ppm chelating agent, in the wash liquor.

The most preferred chelating agent is an aminopolyphosphonate, which is commercially available under the trademark Dequest from Monsanto Company. Examples thereof are Dequest 2000, 2041, and 2060. (See also Bossu U.S. Pat. No. 4,473,507, column 12, line 63 through column 13, line 22, incorporated herein by reference.) A polyphosphonate, such as Dequest 2010, is also suitable for use.

Other preferred non-phosphate containing chelating agents, such as ethylenediaminetetraacetic acid (EDTA) and nitrilotriacetic acid (NTA) may also be suitable for use. Still other new, preferred chelating agents are new propylenediaminetetraacetates, such as Hampshire 1,3 PDTA, from W. R. Grace, and Chel DTPA 100#F, from Ciba Geigy A. G. Mixtures of the foregoing may be suitable.

Additional desirable adjuncts are enzymes (although it may be preferred to also include an enzyme stabilizer). Proteases are one especially preferred class of enzymes. They are preferably selected from alkaline proteases. The term "alkaline," refers to the pH at which the enzymes' activity is optimal. Alkaline proteases are available from a wide variety of sources, and are typically produced from various microorganism (e.g., Bacillus subtilisis). Typical examples of alkaline proteases include Maxatase and Maxacal from International BioSynthetics, Alcalase, Savinase, and Esperase, all available from Novo Industri A/S. See also Stanislowski et al., U.S. Pat. No. 4,511,490, incorporated herein by reference. Further suitable enzymes are amylases, which are carbohydrate-hydrolyzing enzymes. It is also preferred to include mixtures of amylases and proteases. Suitable amylases include Rapidase, from Societe Rapidase, Milezyme from Miles Laboratory, and Maxamyl from International BioSynthetics.

Still other suitable enzymes are cellulases, such as those described in Tai, U.S. Pat. No. 4,479,881, Murata et al., U.S. Pat. No. 4,443,355, Barbesgaard et al., U.S. Pat. No. 4,435,307, and Ohya et al., U.S. Pat. No. 3,983,082, incorporated herein by reference.

Yet other suitable enzymes are lipases, such as those described in Silver, U.S. Pat. No. 3,950,277, and Thom et al., U.S. Pat. No. 4,707,291, incorporated herein by reference.

The hydrolytic enzyme should be present in an amount of about 0.01–5%, more preferably about 0.01–3%, and most preferably about 0.1–2% by weight of the composition. Mixtures of any of the foregoing hydrolases are desirable, especially protease/amylase blends.

Anti-redeposition agents, such as carboxymethylcellulose, are potentially desirable. Foam boosters, such as appropriate anionic surfactants, may be appropriate for inclusion herein. Also, in the case of excess foaming resulting from the use of certain surfactants, anti-foaming agents, such as alkylated polysiloxanes, e.g. dimethylpolysiloxane, would be desirable.

Preferred Granule Size, Density and Shape

Granule particle sizes can range from about 100 $\mu$m to about 1200 $\mu$m, more preferably 150–850 $\mu$m. Granule density will normally range from about 0.5 g/c$^3$ to about 1.0 g/c$^3$, more preferably 0.65 g/c$^3$ to about 0.80 g/c$^3$. A wide variety of granule shapes may be used, including spheres, hearts, moons, stars, clovers, cylindrical sections, and cubic sections.

Applications

Compositions of the invention are useful as or in laundry products, such as bleaching additives, detergents, detergent boosters, detergents with bleach, bleaches, bleaching aids, and stain removers. Among the advantages derived from compositions of the invention are improved cleaning, stain removal, spot removal, whitening, and brightening of treated articles.

Other product applications include household cleaning products, such as hard surface cleaners to be wetted with or dissolved in water prior to use. Exemplary surface cleaners are tile and grout cleaners, bathroom (floor, toilet, and counter) and kitchen (floor, sink, and counter) cleaners. Additionally, kitchen products such as dishwasher detergents with bleach or bleach cleaning and scrubbing pads are contemplated. Among the benefits derived from use of the inventive compositions in such applications are improved stain and spot removal and general cleaning of the treated surfaces to remove food, rust, grime, mildew, mold, and other typical stains found on such surfaces.

Additionally, non-household product applications are contemplated where an effective level of active oxygen generated in situ to treat water is useful. Illustrative of such applications are pool and spa additives, as well as cleaners to remove stains on outdoor concrete, stucco, siding, wood and plastic surfaces.

Preparation of the Nitriles

In general, N-quaternary acetonitrile compounds may be readily prepared from N-acetonitrile precursors by employing selected alkyl halides and using well-known synthetic approaches, such as are described by Menschutkin, *Z. Physik. Chem.*, 5, 589 (1890), and *Z. Physik. Chem.*, 6, 41 (1890); Abraham, *Progr. Phys. Org. Chem.*, 11, 1 (1974);

Arnett, *J. Am. Chem. Soc.*, 102, 5892 (1980); German application DE 05 44 312 212. All these are incorporated by reference.

Compounds having the Formula I structure have a saturated ring formed by a plurality of atoms, broadly ranging from 3 to 9, although preferably containing 6 atoms including the $N_1$ atom. Preparation of these compounds will most conveniently start with a compound already having the formed ring. For example, a number of preparations of inventive nitrites hereinafter described will begin with morpholine (see, e.g., the Formula II structure). An example of three membered rings is aziridine, e.g., N-methylacetonitrile aziridinium; as an example of four membered rings there is azetidine, e.g., N-ethyl-acetonitrile azetidinium; as an example of five membered rings there is pyrrolidine, e.g., N-butylacetonitrile pyrrolidinium; as an example of six membered rings, in addition to morpholine, there is piperidine, e.g., N-methylacetonitrile piperidinium; as an example of seven membered rings there is homopiperidinium; as an example of eight membered rings there is tropane, e.g., N-methylacetonitrile-8-azabicyclo[3.2.1]octane; and, as an example of nine membered rings there is octahydroindole, e.g., N-methylacetonitrile octahydroindolinium.

More particularly, in the preferred method of preparation a suitable amine is reacted with a monoaldehyde or a dialdehyde and with HCN or an alkali metal cyanide in an aqueous medium (Step A) followed by subsequent quaternization (Step B) with an alkylating agent. In Step A, the reaction is preferably either in the pH range from 8 through 14, and the pH value is maintained at not less than 2 in Step B.

Thus, an amine with the formula

is reacted as Step A with a monoaldehyde or a dialdehyde $R^6$—CHO or OHC—$R^5$—CHO, whereby $R^5$ is a chemical bond or a $C_1$ to $C_6$ alkylene bridge or an oxyethylene bridge, and $R^6$ stands for H or $C_1$ to $C_{20}$ alkyl, and with hydrogen cyanide or an alkali metal cyanide in an aqueous medium. Step B is quaternization with an alkylating agent $R^1$—X in an aqueous medium without isolating the intermediate product from Step A. Preferred alkylating agents are dimethylsulfate, diethyl sulfate, a methyl halide, an ethyl halide, dimethyl carbonate, diethyl carbonate, methyl tosylate, ethyl tosylate, methyl mesylate, ethyl mesylate, or a benzyl halide.

In Step A, cyanohydrins, e.g., formaldehyde cyanohydrin, can be formed as by-products from the aldehyde, that is used, and hydrogen cyanide. These cyanohydrins do not react further with the alkylating agent in Step B so that renewed breaking down of the cyanohydrins into aldehyde and hydrogen cyanide in the final product is possible.

Without the procedure in accordance with the invention, Step B usually proceeds in such a way that, as a result of hydrolysis of the added alkylating agent the pH value of the reaction mixture drifts off from the alkaline or neutral region into the strongly acidic region with increasing reaction time. The protonation of the amine nitrogen atom of the glycinonitrile, that has not yet been quaternized, sets in—in competition with alkylation—starting from a certain pH value so that, at the end of the addition of the alkylating agent, no further reaction of the glycinonitrile takes place. Non-quaternized glycinonitrile in the final product can also represent an undesired source of hydrogen cyanide.

Step A generates especially good results if a pH range of 9 through 13 or, especially, 10 through 12, is utilized. In this pH range, the cyanohydrin that is formed is present in an equilibrium with the aldehyde and the hydrogen cyanide so that the re-formed adducts can react to completion with the amine to give glycinonitrile.

If one also uses an excess of amine that amounts to about 2 through 20 mole % or, especially, about 3 through 10 mole % or, most particularly of all, about 4 through 7 mole %, based on the quantity of the hydrogen cyanide or alkali metal cyanide that is used, then one achieves even more extensive suppression of hydrogen cyanide and ancillary components, that liberate hydrogen cyanide, in the final product.

Step B generates especially good results if the pH values are not reduced below 2.5 and, especially, not below 3. An optimum pH range for the quaternization of Step B is 2.5 through 5 or, especially, 3 through 4.

Use is also made of an excess of alkylating agent that amounts to 10 to 40 mole % or, especially, 15 to 25 mole % based on the quantity of amine that is used in Step A, then one achieves still more extensive suppression of the hydrogen cyanide and the subsidiary components, that liberate hydrogen cyanide, in the final product.

Once the nitrites are prepared in quaternized form, formation of the preferred bisulfate or sulfate form preferably is by heating an alkyl sulfate form, in an acid aqueous solution. For example, a suitable elevated temperature is about 40° C. to about 150° C., more preferably about 70° C. to about 110° C. The acid aqueous solution may have a pH in the range of about −1 to 6, more preferably from about 0 to 3, with the heating being for a period of about 1 to 50 hours.

Aspects of the invention will now be illustrated by the following examples. It will be understood that these examples are intended to illustrate, and not to limit, the invention.

EXAMPLE 1

527.2 g (6.05 moles) of morpholine were introduced into the reaction vessel and cooled to 10° C. Within a period of one hour, 600 g (6.0 moles) of formaldehyde (30% by weight) were then metered in. The addition of 161.6 g (5.94 moles) of hydrogen cyanide (99.25% by weight) started half an hour after the start of the addition of formaldehyde. The time of addition amounted to 1 hour. During the addition, the temperature was allowed to rise to 35° C. and stirring then took place for a further hour at 35° C. Cooling to 30° C. then took place and 927.8 g (7.35 moles) of dimethylsulfate (DMS) were added within 2 hours at 30° C. During the DMS addition, the pH value fell into the acidic region starting from 8. At pH 3.5, the pH-regulated addition of aqueous caustic soda (25% by weight) was counter-controlled so that the pH remained constant at 3.5 during the remaining addition time and the following post-reaction time of 3 hour at 30° C. The mixture was then heated to 50° C. and the pH value was allowed to fall in this connection. After 1 hour at 50° C., the excess DMS was completely destroyed. The pH value was then 1.

| Analytical results: | |
|---|---|
| HCN | 0 ppm |
| formaldehyde cyanohydrin | 74 ppm |
| morpholinoacetonitrile | 55 ppm |

(Molar ratio HCN:CH$_2$O:morpholine = 1:1.01:1.02; molar ratio morpholine:dimethylsulfate = 1:1.21)

EXAMPLE 2

527.2 g (6.05 moles) of morpholine were introduced into the reaction vessel and cooled to 10° C. 6.6 g of aqueous caustic soda (20% by weight) were added in order to raise the pH value. Within a period of one hour, 600 g (6.0 moles) of formaldehyde (30% by-weight) were then metered in. The addition of 161.6 g (5.4 moles) of hydrogen cyanide (99.25% by weight) started half an hour after the start of the addition of formaldehyde. The time of addition amounted to 1 hour. During the addition, the temperature was allowed to rise to 35° C. and stirring then took place for a further hour at 35° C. The pH value amounted to 11.4 at the end of this part of the synthesis. The pH was then adjusted to 8–8.2 with sulfuric acid. Cooling to 30° C. then took place and 932.4 g (7.4 moles) of dimethylsulfate (DMS) were added within 2 hours at 30° C. During the DMS addition, the pH value fell into the acidic region starting from 8. At pH 3.5, the pH-regulated addition of aqueous caustic soda (25% by weight) was counter-controlled so that the pH remained constant at 3.5 during the remaining addition time and the following post-reaction time of 3 hour at 30° C. The mixture was then heated to 50° C. and the pH value was allowed to fall in this connection. After 1 hour at 50° C., the excess DMS was completely destroyed. The pH value was then 1.

| Analytical results: | |
|---|---|
| HCN | 0 ppm |
| formaldehyde cyanohydrin | 10 ppm |
| morpholinoacetonitrile | 20 ppm |

(Molar ratio HCN:CH$_2$O:morpholine = 1:1.01:1.02; molar ratio morpholine:dimethylsulfate = 1:1.22)

EXAMPLE 3

537.2 g (6.17 moles) of morpholine were introduced into the reaction vessel and cooled to 10° C. 6.7 g of aqueous caustic soda (20% by weight) were added in order to raise the pH value. Within a period of one hour, 600 g (6.0 moles) of formaldehyde (30% by weight) were then metered in. The addition of 161.6 g (5.94 moles) of hydrogen cyanide (99.25% by weight) started half an hour after the start of the addition of formaldehyde. The time of addition amounted to 1 hour. During the addition, the temperature was allowed to rise to 35° C. and stirring then took place for a further hour at 35° C. The pH value amounted to 11.8 at the end of this part of the synthesis. The pH was then adjusted to 8–8.2 with sulfuric acid. Cooling to 30° C. then took place and 940 g (7.46 moles) of dimethylsulfate (DMS) were added at 30° C. within 2 hours. During the DMS addition, the pH value fell into the acidic region starting from 8. At pH 3.5, the pH-regulated addition of aqueous caustic soda (25% by weight) was counter-controlled so that the pH remained constant at 3.5 during the remaining addition time and the following post-reaction time of 3 hour at 30° C. The addition of caustic soda took place with good mixing (stirring conditions of 800 revolutions/minute). The mixture was then heated to 50° C. and the pH value was allowed to fall in this connection. After 1 hour at 50° C., the excess DMS was completely destroyed. The pH value was then 1.

| Analytical results: | |
|---|---|
| HCN | 0 ppm |
| formaldehyde cyanohydrin | 0 ppm |
| morpholinoacetonitrile | 20 ppm |
| N-methylmorpholinium acetonitrile methylsulfate | 58.0% by wt. |
| N-methylmorpholinium acetamide methylsulfate | 3.0% by wt. |

(Molar ratio HCN:CH$_2$O:morpholine = 1:1.01:1.04; molar ratio morpholine:dimethylsulfate = 1:1.21)

Example 4 illustrates another aspect of the invention, which is the preparation of substantially solid bisulfate salts, such as to prepare MMABS.

EXAMPLE 4

The methylsulfate liquid, such as in any of Examples 1–3, was acidified to a pH of 0.1–1 followed by heating the resulting liquid under a slight vacuum (700–1000 mbar) in a vented container at temperatures of 90–110° C. for 3–5 hours.

The resulting bisulfate converted liquid may then be crystallized and purified for recovery of crystalline nitrile salt, may be dried directly onto a support/carrier to produce an amorphous salt, or may be redissolved after crystallization and then prepared in granule form. One preferred approach to promote the crystallization or precipitation may be via addition of a "seed crystal," which serves as a growth location for crystal formation. This seed crystal can be, but is not limited to, precipitated or fumed silica, or a sample of the bisulfate crystal salt itself. Another preferred approach is to allow the salt solution to precipitate out by reducing the crystal solubility via cooling over time.

EXAMPLE 5

96 kg of MMAMS liquid (48.5% active) were acidified with 6.7 kg of sulfuric acid (50%) at 20° C. and subsequently heated to 110° C. for 4½ hours after which the solution was cooled to 30° C. over an 18 hour period. The resulting slurry was then washed with water and filtrated to yield the resulting bisulfate crystal (61.7 kg)

When one wishes to prepare the nitrile salts in granule form, such can be by use of various methods known to the art, such as fluid bed, agglomerating, spray coating, or melt mixing approaches, preferably at levels of about 5–40 wt. % of the starting particulate weight. These granules may have the nitrile salts carried on solid particulate or may have the nitrile salt coated by or admixed with solid particulate.

Conditions for coating preferably are whereby the temperature during coating is less than about 50° C. while the coating material is sprayed as a melt or dispersion onto the salt surface thereby coating or encapsulating the salt core. Example 6 illustrates different forms of the salt core and a variety of preferred coating materials. Anticipated coating materials include film-forming polymers, fatty acids, soaps, and other solid surfactants having a melting point above 40° C.

| Nitrile Salt Core | Preferred Coatings Materials |
|---|---|
| Purified crystal salt | PLURONIC 6800[1] |
| Amorphous compacted salt | PLURONIC 10500[1] |
| Amorphous agglomerated salt | PLURIOL E 6000[1] |
| Amorphous acidified salt | SOKALAN CP5[1] |
| | LUWAX V[1] |
| | Polyvinyl alcohol |
| | Palmitic acid |
| | Paraffin |
| | Calcium Alginate |
| | POLIGEN WE3[1] |
| | DIOFAN 193D[1] |

[1]Commercially available from BASF AG, Germany.

Particularly preferred coating materials are PLURIOL E6000 and LUWAX V. (PLURONIC is a trademark for a series of poly(oxyethylene-co-oxypropylene) block copolymers.)

EXAMPLE 7
Preparation of a Solid MMAMS/silicic Acid/surfactant Composition Using a Stirring Process 3.4 kg of a highly dispersed silicic acid with a total surface area of approximately 450 m²/g and an average particle size of approximately 8 mm (SIPERNAT® 50 S from the Degussa firm) and, additionally, 2.3 kg of a tallow-based fatty alcohol that had been reacted with 25 mol of ethylene oxide (Lutensol® AT 25 from the BASF firm) were stirred into 24.3 kg of a 70% by weight aqueous solution of N-methylmorpholinium acetonitrile methylsulfate (MMAMS). The liquid mixture was concentrated by evaporation in a paddle-type vacuum dryer at approximately 10 mbar and a wall temperature of approximately 80° C. until a solid was formed that was capable of flowing (residual water content <1% by weight). After cooling, 20 kg of the solid composition were removed. The powder was compacted by means of a conventional compactor to give flakes and the flakes were then broken up in a conventional sieve granulator and sieved to give a usable fraction of 400 to 1200 mm average size.

EXAMPLE 8
Manufacture of a Solid MMAMS/silicic Acid/surfactant Composition by Means of a Spray Process 24.3 kg of a 70% by weight MMAMS solution were sprayed onto 31.6 kg of the highly dispersed silicic acid that was described in Example 7. The crumbly mixture was dried in a paddle-type vacuum dryer at approximately 10 mbar and a wall temperature of approximately 80° C. until a fine solid was formed that was capable of flowing (residual water content <1% by weight). The product was then agglomerated in a mixture with a melt of 2.3 kg of the surfactant that was designated in Example 7. Final processing to give a usable fraction of 400 to 1200 mm was carried out analogously to Example 7.

EXAMPLE 9
Effect of Carrier Materials and Surfactants on the Hygroscopic Characteristics or, as the Case May be, the Flow Characteristics of MMAMS In order to ascertain the effect of ancillary substances on the hygroscopic characteristics or, as the case may be, the flow characteristics of MMAMS, three different samples were prepared in the paddle-type dryer and were then stored in a desiccator at room temperature and a relative atmospheric humidity of 76%.

| Sample 1: | 2100 g | MMAMS (solid) |
|---|---|---|
| Sample 2: | 3100 g | MMAMS (solid) |
| | 400 g | SIPERNAT 50 S |
| Sample 3: | 3100 g | MMAMS (solid) |
| | 400 g | SIPERNAT 50 S |
| | 233 g | Lutensol AT 25 |

All the samples were prepared from a 70% by weight aqueous MMAMS solution analogously to Example 7 and were dried at 80° C. and 10 mbar in a paddle-type vacuum dryer with a volume of 5 liters until no more condensate was generated.

In the case of Examples 8 and 9, one obtained a powder-type solid, that was capable of flowing after drying, with water contents of 0.74% by weight or 0.45% by weight, respectively; the MMAMS without the ancillary substances (sample 1) led to a wax-like, crumbly solid with a water content of 0.63% by weight.

These solids were then ground to the same average particle size and were stored in the desiccator. The results are presented in the following Table 2.

It is clearly seen that solid MMAMS is obtained in a high concentration and is stable on storage over a long period of time at a relative atmospheric humidity of 76% only as a result of the addition of the designated ancillary substances.

TABLE 2

| Storage time | 0 hr | 17 hrs | 41 hrs | 113 hrs |
|---|---|---|---|---|
| Water Content % Sample 1 | 0.63 | 5.23 | 9.23 | 9.8 |
| Ability to Flow Sample 1 | capable of flowing | baked on | partially detached | partially detached |
| Water Content % Sample 2 | 0.74 | 5.04 | 9.04 | 11.44 |
| Ability to Flow Sample 2 | capable of flowing | capable of flowing | small clumps | slightly baked on |
| Water Content % Sample 3 | 0.45 | 3.65 | 6.15 | 8.55 |
| Ability to Flow Sample 3 | capable of flowing | capable of flowing | capable of flowing | capable of flowing |

EXAMPLE 10
Effect of Carrier Materials on the Storage Stability and Dye Damage Characteristics Samples of MMAMS on various carriers were prepared and put in a bleaching composition to determine any benefit in storage stability or dye damage.

Storage Stability

The MMA methylsulfate has greater storage stability on an inert support, such as zeolite or clay. The presence of an acid sink, such as HLAS (alkylbenzenesulfonic acid), also enhances stability.

The MMA methylsulfate aqueous solution (3.6 g of 45%) was added to 38.5 q of sodium carbonate containing 5.0 g of sodium perborate monohydrate and the solid dried. This was compared to first adding the MMA methylsulfate to 6 parts of zeolite 4A (Valfour 100 from PQ Corp.) and then adding to the sodium carbonate/perborate mixture. The MMA methylsulfate could also be mixed with 6 parts of clay (Attapulgite L96117 from Oil-Dry Corp.) and then added to the sodium carbonate/perborate mixture. The MMA methylsulfate was also mixed with 2 parts of the same clay.

The results below in Table 3 show the surprisingly enhanced stability when the MMA methylsulfate is incorporated into the inventive supports.

TABLE 3

| MMA substrate in Carbonate/Perborate | % MMA Active after 1 wk Storage at 80° F/80% RH |
|---|---|
| MMAMS | 0% |
| MMAMS/Zeolite = 1/6 | 98% |
| MMAMS/HLAS/Zeolite = 1/2/6 | 100% |
| MMAMS/Clay = 1/6 | 100% |
| MMAMS/Clay = 1/2 | 100% |

Dye Damage Testing

The amount of MMAMS representing 5% of the base (sodium carbonate/perborate mixture) was placed on a diagnostic fabric (Brown 100% cotton dyed with Fast Orange RD, Direct Brown 5R and Rapideger Red LD). The MMAMS was covered with the base and then 10 ml of deionized water was applied. After 10 minutes, the fabric was rinsed and allowed to dry. The dye damage was visually evaluated on a 0 to 10 scale, where 0 represents no visible damage. The same samples as prepared above for the stability testing were used. The results again show the benefit of adding MMAMS to an inert support, with or without an acidic co-agent.

| Nitrile Substrate | Dye Damage |
|---|---|
| Aqueous MMA methylsulfate | 10 |
| MMAMS/Zeolite = 1/6 | 3 |
| MMAMS/HLAS/Zeolite = 1/2/6 | 1 |
| MMAMS/Clay = 1/6 | 1 |

It is to be understood that while the invention has been described above in conjunction with preferred specific embodiments, the description and examples are intended to illustrate and not limit the scope of the invention, which is defined by the scope of the appended claims.

It is claimed:

1. A process for the preparation of a compound having the structure of Formula I

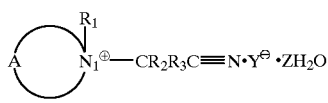

FORMULA I wherein A is a saturated ring formed by a plurality of atoms in addition to the $N_1$ atom, the saturated ring atoms including at least one carbon atom and at least one heteroatom in addition to the $N_1$ atom, the said heteroatom selected from the group consisting of O, S, and N atoms, the substituent $R_1$ bound to the $N_1$ atom of the Formula I structure is (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, or (e) —$CR_2R_3C\equiv N$ where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$, the $R_2$ and $R_3$ substituents being each H, a $C_{1-24}$ alkyl, cycloalkyl, or alkaryl, or a repeating or nonrepeating alkoxyl or alkoxylated alcohol where the alkoxy unit is $C_{2-4}$, Z is a value in the range of 0 to 10, and wherein Y is counterion, comprising the steps of:

reacting a heterocyclic amine

with (1) a monoaldehyde $R^6$—CHO or a dialdehyde OHC—$R^5$—CHO whereby $R^5$ is a chemical bond or a $C_1$ to $C_6$ alkylene bridge and $R^6$ stands for H or $C_1$ to $C_{20}$ alkyl, and (2) hydrogen cyanide or an alkali metal cyanide in an aqueous medium (Step A) wherein the carrying out of Step A includes using an excess of the amine that amounts to about 2 mole % to about 20 mole % based on the quantity of hydrogen cyanide or alkali metal cyanide; and, quaternizing the so reacted heterocyclic amine with an alkylating agent $R^1$—X (Step B), whereby Step A is carried out in a pH range of from 8 to 14 and Step B is carried out at a pH of not less than about 2.

2. The process as in claim 1 wherein A of Formula I is a saturated ring formed by four carbon atoms and one oxygen atom in addition to the $N_1$ atom.

3. The process as in claim 1 wherein carrying out Step B at a pH of not less than about 2 includes using an excess of the alkylating agent that amounts to about 10 mole % to about 40 mole % based on the quantity of the heterocyclic amine.

4. The process as in claim 1, 2, or 3 whereby the alkylating agent is dimethylsulfate, diethyl sulfate, a methyl halide, an ethyl halide, dimethyl carbonate, diethyl carbonate, methyl tosylate, ethyl tosylate, methyl mesylate, ethyl mesylate, or a benzyl halide.

5. The process as in claim 4 whereby the alkylating agent is dimethylsulfate.

6. The process as in claim 5 further comprising converting the methylsulfate counterion to bisulfate or sulfate.

7. The process for preparing a compound with the structure of Formula II substantially free of hydrogen cyanide

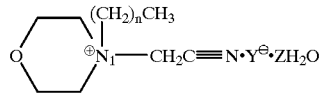

FORMULA II wherein n is 0 to 24 and Y is counterion, comprising the steps of:

reacting morpholine with (1) a monoaldehyde $R^6$—CHO or a dialdehyde OHC—$R^5$—CHO whereby $R^5$ is a chemical bond or a $C_1$ to $C_6$ alkylene bridge or oxyethylene bridge and $R^6$ stands for H or $C_1$ to $C_{20}$ alkyl, and (2) hydrogen cyanide or an alkali metal cyanide in an aqueous medium (Step A) at a pH range from 8 to 14 using an excess of the amine that amounts to about 2 mole % to about 20 mole % based on the quantity of hydrogen cyanide or alkali metal cyanide; and, quaternizing the so reacted morpholine with an alkylating agent $R^1$—X, wherein $R^1$ is $C_1$–$C_{24}$ alkyl (Step B) is carried out at a pH effectively controlled to substantially prevent formation of a protonated morpholine reaction intermediate.

8. The process as in claim 7 wherein the pH is maintained during Step B at not less than about 2.

9. The process as in claim 8 whereby the alkylating agent is dimethylsulfate.

* * * * *